(12) United States Patent
Harding

(10) Patent No.: US 12,357,208 B2
(45) Date of Patent: Jul. 15, 2025

(54) MULTI-CHAMBER BLOOD COLLECTION DEVICE AND RELATED SYSTEMS AND METHODS

(71) Applicant: Becton, Dickinson and Company, Franklin Lakes, NJ (US)

(72) Inventor: Weston F. Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/063,241

(22) Filed: Oct. 5, 2020

(65) Prior Publication Data

US 2021/0113127 A1    Apr. 22, 2021

Related U.S. Application Data

(60) Provisional application No. 62/956,543, filed on Jan. 2, 2020, provisional application No. 62/916,014, filed on Oct. 16, 2019.

(51) Int. Cl.
*A61B 5/15* (2006.01)
*A61B 5/154* (2006.01)

(52) U.S. Cl.
CPC .. *A61B 5/150251* (2013.01); *A61B 5/150236* (2013.01); *A61B 5/154* (2013.01); *A61B 5/15003* (2013.01); *A61B 5/150351* (2013.01)

(58) Field of Classification Search
CPC .......... A61B 5/150251; A61B 5/15003; A61B 5/150351; A61B 5/150236; A61B 5/15074; A61B 5/154
See application file for complete search history.

(56) References Cited

U.S. PATENT DOCUMENTS 4,037,464 A * 7/1977 Wenander ............. B01L 3/0217
                                                       422/550
4,133,863 A    1/1979 Koenig
(Continued)

FOREIGN PATENT DOCUMENTS

CN    102353569 A    2/2012
CN    104939844      9/2015
(Continued)

OTHER PUBLICATIONS

BD Life Sciences—Preanalytical Systems Product Catalog Jun. 2015 (Year: 2015).*
(Continued)

*Primary Examiner* — Jason M Sims
*Assistant Examiner* — Kyle W. Kretzer
(74) *Attorney, Agent, or Firm* — The Webb Law Firm

(57) ABSTRACT

A blood collection device may include a tubular container, which may include a closed end and an open end opposite the closed end. The blood collection device may include a plug sealing the open end and a partition within the tubular container. The partition may separate the tubular container into a first chamber and a second chamber. The first chamber and the second chamber may be evacuated such that a pressure within the first chamber and a pressure within the second chamber are lower than ambient pressure and equal to each other. In response to blood being drawn into the first chamber, the pressure within the first chamber may increase, and the partition may slide towards the closed end such that a size of the first chamber increases and a size of the second chamber decreases.

2 Claims, 5 Drawing Sheets

(56) References Cited

U.S. PATENT DOCUMENTS

| | | | |
|---|---|---|---|
| 4,492,634 A | 1/1985 | Villa-Real | |
| 5,882,318 A | 3/1999 | Boyde | |
| 6,409,528 B1 | 6/2002 | Bodnar | |
| 2002/0153316 A1* | 10/2002 | Nanba | A61B 5/150022 210/650 |
| 2004/0013575 A1 | 1/2004 | Stevens et al. | |
| 2005/0059163 A1 | 3/2005 | Dastane et al. | |
| 2010/0168614 A1 | 7/2010 | Crawford | |
| 2012/0149004 A1 | 6/2012 | Gelfand et al. | |
| 2015/0018715 A1* | 1/2015 | Walterspiel | A61B 5/150251 422/570 |

FOREIGN PATENT DOCUMENTS

| | | | |
|---|---|---|---|
| CN | 105581801 A | * | 5/2016 |
| CN | 103384496 B | | 10/2016 |
| CN | 107677431 A | * | 2/2018 |
| CN | 109199406 A | * | 1/2019 |
| DE | 2603777 | | 8/1976 |
| DE | 8625508 U1 | | 1/1988 |
| JP | 2001321366 A | | 11/2001 |
| JP | 2005253538 A | * | 9/2005 |
| JP | 2007501398 A | | 1/2007 |
| WO | 94/07415 | | 4/1994 |
| WO | 03/097237 | | 11/2003 |
| WO | 2011/069145 | | 6/2011 |
| WO | 2012/075407 | | 6/2012 |

OTHER PUBLICATIONS

BD Life Sciences—Preanlytical Systems Product Catalog Jun. 2015 (Year: 2015).*

* cited by examiner

MULTI-CHAMBER BLOOD COLLECTION DEVICE AND RELATED SYSTEMS AND METHODS

RELATED APPLICATIONS

This application claims the benefit of U.S. Provisional Application No. 62/916,014, filed Oct. 16, 2019, and entitled MULTI-CHAMBER BLOOD COLLECTION DEVICE AND RELATED SYSTEMS AND METHODS, and U.S. Provisional Application No. 62/956,543, filed Jan. 2, 2020, and entitled MULTI-CHAMBER BLOOD COLLECTION DEVICE AND RELATED SYSTEMS AND METHODS, both are incorporated herein in their entirety.

BACKGROUND

An evacuated blood collection tube includes a test tube with a rubber stopper at one end. The evacuated blood collection tube has had all or a portion of air removed from the test tube so pressure within the evacuated blood collection tube is lower than ambient pressure. Such an evacuated blood collection tube is often referred to as an internal vacuum or a vacuum tube. A commonly used evacuated blood collection tube is a VACUTAINER blood collection tube, available from Becton Dickinson & Company.

To collect a blood sample from a patient, a clinician first gains access to the patient's vein with either a needle or a catheter. An adapter coupled to the needle or the catheter. The adapter includes an additional needle that penetrates the rubber stopper of the evacuated blood collection tube. When the rubber stopper is penetrated, a pressure in the vein is higher than a pressure in the evacuated blood collection tube, which pushes blood into the evacuated blood collection tube, thus filling the evacuated blood collection tube with blood. A vacuum within the evacuated blood collection tube decreases as the evacuated blood collection tube fills until the pressure in the evacuated blood collection tube equalizes with the pressure in the vein, and the flow of blood stops. As blood is drawn into the evacuated blood collection tube, red blood cells are in a high shear stress state and susceptible to hemolysis.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a multi-chamber blood collection device, as well as related systems and methods. In some embodiments, a blood collection device may include a tubular container, which may include a closed end and an open end opposite the closed end. In some embodiments, the blood collection device may include a plug sealing the open end and a partition within the tubular container between the open end and the closed end. In some embodiments, the partition may separate the tubular container into a first chamber and a second chamber. In some embodiments, the first chamber and the second chamber may be evacuated such that a pressure within the first chamber and a pressure within the second chamber are lower than ambient pressure. In some embodiments, the partition may be impermeable to air, and the first chamber and the second chamber may be airtight.

In some embodiments, the first chamber may be proximate the plug and the second chamber may be proximate the closed end. In some embodiments, the pressure within the first chamber and the pressure within the second chamber may be equal. In some embodiments, a size of the first chamber and a size of the second chamber may be approximately equal. In some embodiments, the partition may be disposed generally in a middle of a length of the tubular container.

In some embodiments, in response to blood being drawn into the first chamber, the pressure within the first chamber may increase, and the partition may move towards the closed end such that the size of the first chamber increases and the size of the second chamber decreases.

In some embodiments, the partition may include a plug. In some embodiments, the partition may be constructed of rubber or another suitable material. In some embodiments, an outer circumference of a body of the partition may contact the tubular container to form a seal. In other embodiments, the partition may include an O-ring, which may be coupled to an outer perimeter of the body of the partition and may contact the tubular container to form a seal.

In some embodiments, a lubricant may be disposed between the partition and the tubular container. In some embodiments, the partition may include an inner portion and an outer portion, which may surround the inner portion. In some embodiments, the inner portion has a first durometer, and the outer portion has a second durometer. In some embodiments, the first durometer may be greater than the second durometer.

In some embodiments, the blood collection device may include another partition and a third chamber. In some embodiments, the second chamber may be disposed between the partition and the other partition. In some embodiments, the third chamber may be evacuated such that a pressure within the third chamber is lower than ambient pressure and equal to the pressure within the first chamber and the pressure within the second chamber. In some embodiments, the other partition may be impermeable to air and the third chamber is airtight.

In some embodiments, a method of blood collection may include inserting a needle of a blood collection set into a vasculature of a patient and coupling a blood collection device to the blood collection set by inserting a cannula into the blood collection device. In some embodiments, in response to coupling the blood collection device to the blood collection set the pressure within the first chamber may increase, the partition may slide towards the closed end such that a size of the first chamber increases and a size of the second chamber decreases.

In some embodiments, the blood collection set may include one or more of the following: a hub, a needle, an extension tube, and an adapter. In some embodiments, the needle may be secured within the hub and/or extend distally beyond the hub. In some embodiments, the adapter may include the cannula and an elastomeric sheath. In some embodiments, the elastomeric sheath may be coupled to the adapter and/or may envelop the cannula. In some embodiments, the extension tube may include a distal end coupled to the hub and a proximal end coupled to the adapter.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1C:
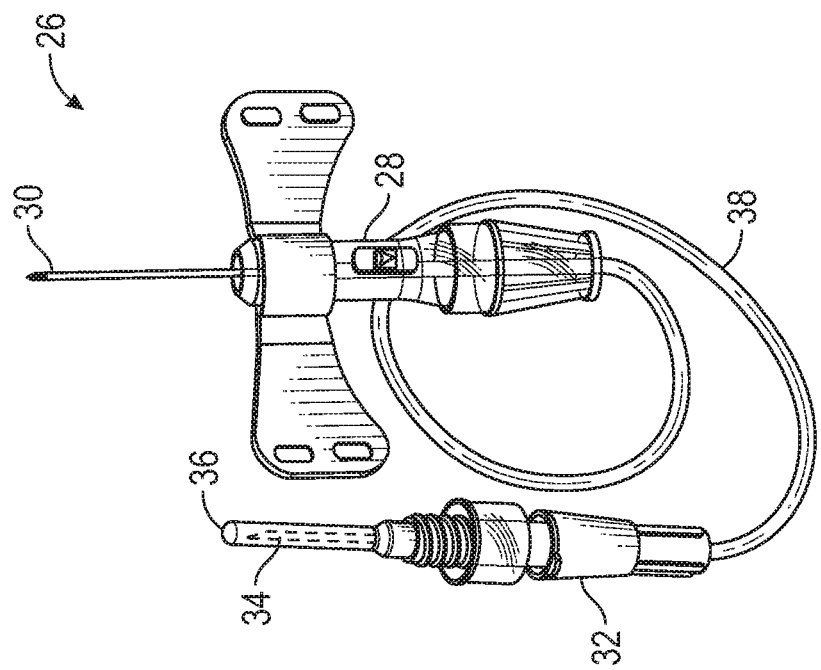
FIG. 1C is an upper perspective view of an example blood collection set, according to some embodiments.
Figure 1B:
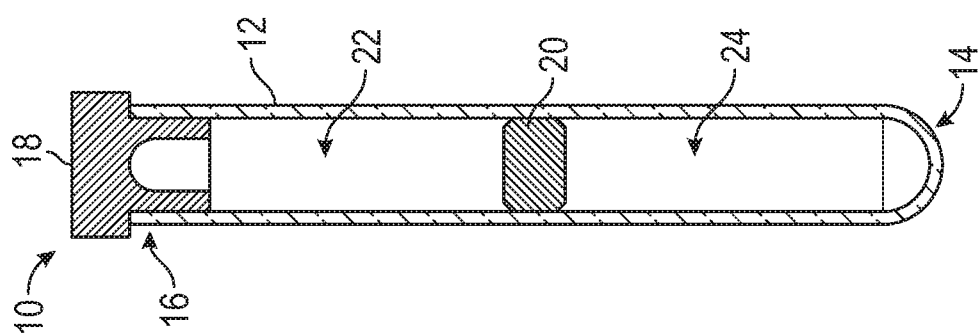
FIG. 1B is a cross-sectional view of the blood collection device of FIG. 1A, according to some embodiments.
Figure 1A:
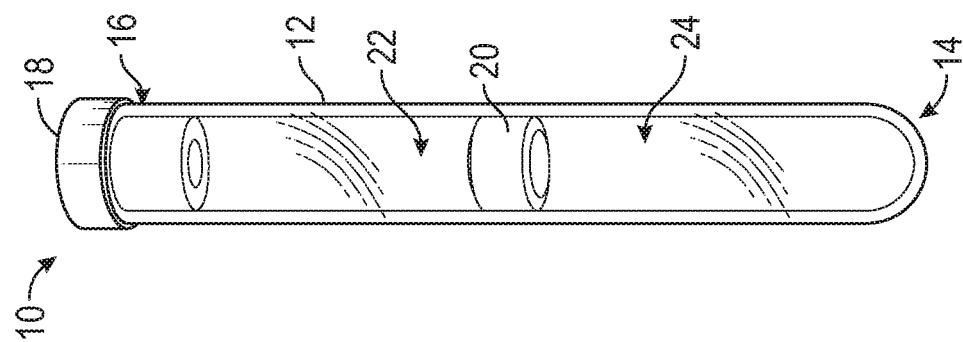
FIG. 1A is a lower perspective view of an example blood collection device, according to some embodiments.

Referring now to FIGS. 1A-1B, in some embodiments, a blood collection device 10 may include a tubular container 12, which may include a closed end 14 and/or an open end 16 opposite the closed end 14. In some embodiments, the tubular container 12 may include a test tube. In some embodiments, the blood collection device 10 may include a plug 18 sealing the open end 16. In some embodiments, the plug 18 may act as a hermetic seal to ensure the blood collection device 10 is airtight. In some embodiments, the blood collection device 10 may include a partition 20 within the tubular container 12. In some embodiments, the partition 20 may be disposed between the open end 16 and the closed end 14.

In some embodiments, the partition 20 may separate the tubular container 12 into a first chamber 22 and a second chamber 24. In some embodiments, the first chamber 22 and the second chamber 24 may be evacuated, either partially or fully, such that a pressure within the first chamber 22 and a pressure within the second chamber 24 are lower than ambient or atmospheric pressure. In some embodiments, the pressure within the first chamber 22 and the pressure within the second chamber 24 may be equal. In some embodiments, the size of the first chamber 22 and the size of the second chamber 24 may be approximately equal. In some embodiments, size may correspond to volume.

In some embodiments, the partition 20 may be impermeable to air and/or liquid. In some embodiments, the first chamber 22 and the second chamber 24 may be airtight. In some embodiments, the first chamber 22 may be proximate the plug 18. In some embodiments, the second chamber 24 may be proximate the closed end 14 of the tubular container 12.

In some embodiments, the tubular container 12 may be constructed of glass, a rigid polymeric material, plastic, or another suitable material. In some embodiments, the plug 18 may be constructed of an elastomeric material or another suitable material that provides a hermetic seal before and after being punctured by a needle.

Referring now to FIG. 1C, a blood collection set 26 is illustrated, according to some embodiments. In some embodiments, the blood collection set 26 may include any suitable blood collection set configured to receive the blood collection device 10. In some embodiments, the blood collection set 26 may include a needle set, which may be winged. For example, the needle set may include the BD VACUTAINER SAFETY-LOK Blood Collection Set. In some embodiments, the needle set may include any suitable needle set known in the art.

In some embodiments, the blood collection set 26 may include a hub 28 and a needle 30. In some embodiments, the needle 30 may include a sharp distal tip. In some embodiments, the needle 30 may be secured within the hub 28. In some embodiments, the needle 30 may extend distally beyond the hub 28. In some embodiments, the blood collection set 26 may include an adapter 32, which may include a cannula 34 and/or an elastomeric sheath 36. In some embodiments, the blood collection set 26 may include an extension tube 38, which may extend between the adapter 32 and the hub 28. In some embodiments, the adapter 32 may be coupled directed to the hub 28. In some embodiments, the adapter 32 may include any suitable adapter known in the art.

In some embodiments, the elastomeric sheath 36 may be coupled to the adapter 32 and/or a proximal end of the cannula 34 may be enveloped within the elastomeric sheath 36. In some embodiments, the elastomeric sheath 36 may include an open distal end and a closed proximal end. In some embodiments, in response to the blood collection set 26 pushing the elastomeric sheath 36 distally towards the adapter 32, the cannula 34 may pierce the elastomeric sheath 36 and the plug 18 and may be inserted into the first chamber 22.

In some embodiments, the blood collection set 26 may include a catheter assembly. In these embodiments, a catheter (not illustrated) may extend distally from a distal end of the hub 28. In some embodiments, the catheter may include a peripheral intravenous catheter (PIVC), a peripherally inserted central catheter (PICC), or a midline catheter. In some embodiments, the catheter assembly may include any suitable catheter assembly known in the art. In some embodiments, the catheter assembly may include an over-the-needle catheter, which may be mounted over the needle 30. In some embodiments, the catheter and the needle 30 may be assembled such that the distal tip of the needle 30 extends beyond the distal tip of the catheter with the bevel of the needle facing up away from skin of the patient.

In some embodiments, the needle 30 of the blood collection set 26 may be inserted into the vasculature of the patient. In some embodiments, the needle 30 may be inserted at a shallow angle through the skin into the vasculature of the patient. In some embodiments, in response to the needle 30 being inserted into the vasculature of the patient, blood may flow through the needle 30, the hub 28, and the extension tube 38. In some embodiments, blood may then flow into the adapter 32. In some embodiments, in response to catheter being inserted into the vasculature of the patient, blood may flow through the catheter, the hub 28, and the extension tube 38, and then into the adapter 32.

Figures 1D, 1E:
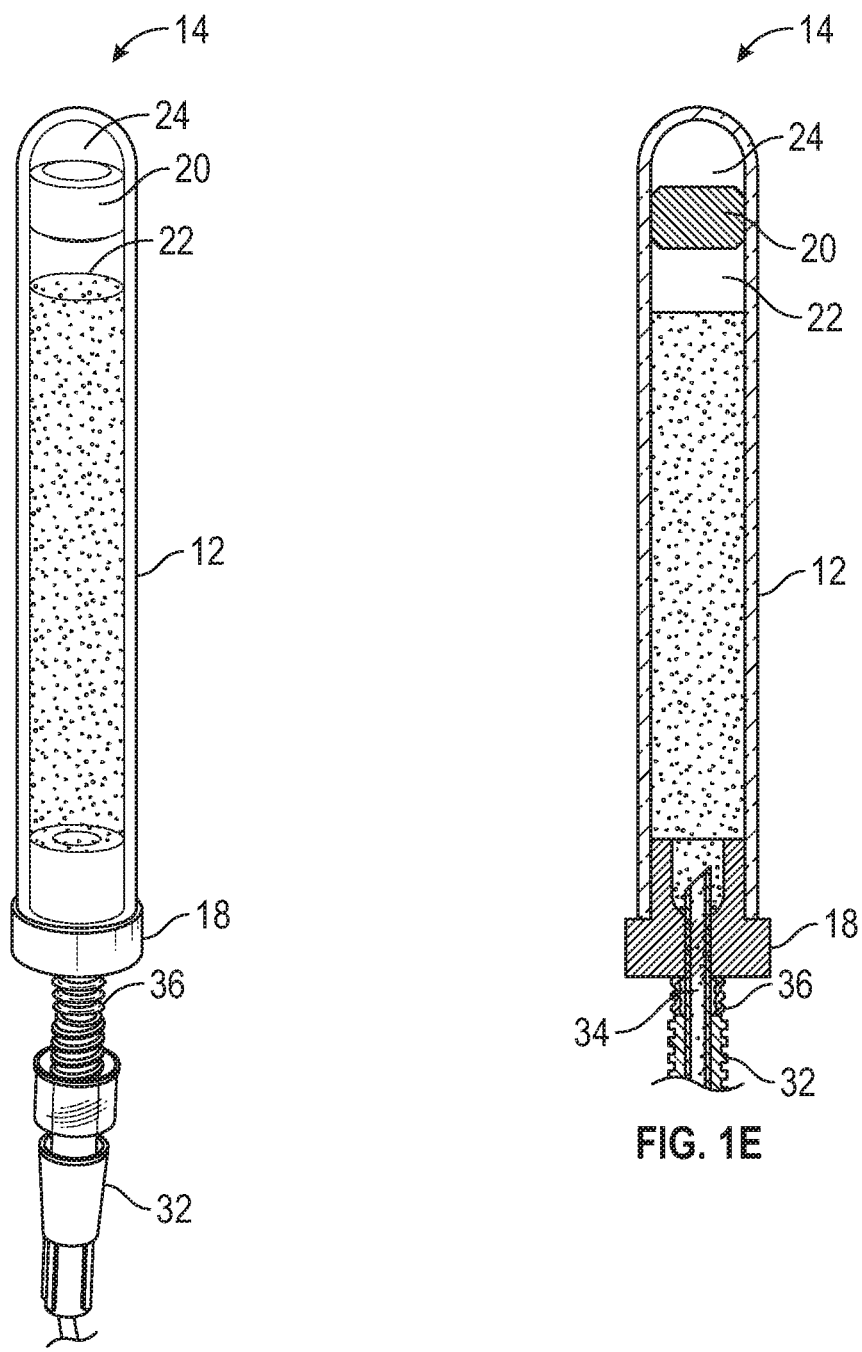
FIG. 1D is an upper perspective view of the blood collection device of FIG. 1A coupled to the blood collection set of FIG. 1C, according to some embodiments.
FIG. 1E is a cross-sectional view of the blood collection set of FIG. 1D, according to some embodiments.

Referring now to FIGS. 1D-1E, in some embodiments, the blood collection device 10 may be coupled to the blood collection set 26 by inserting the cannula 34 into the blood collection device 10. In some embodiments, the blood collection device 10 may be coupled to the blood collection set 26 after the blood collection set 26 is positioned within the vasculature. In some embodiments, when the plug 18 is penetrated by the cannula 34, pressure in the vasculature may push blood into the first chamber 22, which may be at a lower pressure than the vasculature.

In some embodiments, the partition 20 may facilitate collection of a full blood sample while reducing a risk of hemolysis. In some embodiments, a vacuum within the first chamber 22 may decrease more quickly than it would otherwise, due to the partition 20. In some embodiments, the partition 20 may reduce a time at which blood stays in a high shear stress state by facilitating a faster drop in a vacuum level within the first chamber 22. In some embodiments, the quick drop in the vacuum level within the first chamber 22 may be due to the size of the first chamber 22 being only a portion of a size or about half the size of the tubular container 12.

In some embodiments, in response to the vacuum within the first chamber 22 dropping to a predetermined level, a pressure differential between the first chamber 22 and the second chamber 24 may slide the partition 20 towards the closed end 14. In some embodiments, in response to the partition 20 sliding towards the closed end 14, the size of the first chamber 22 may increase, effectively adding more vacuum to the first chamber 22. In some embodiments, in response to the partition 20 sliding towards the closed end 14, the size of the second chamber 24 may decrease. In some embodiments, blood may stop flowing into the blood collection device 10 in response to the partition 20 sliding adjacent or proximate the closed end 14 and the vacuum within the first chamber 22 being depleted due to the first chamber 22 being filled with blood.

Figure 2A:
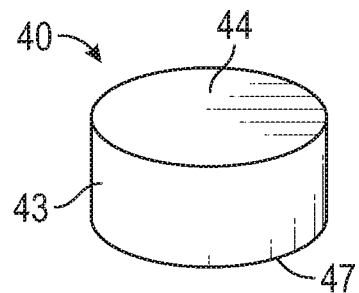
FIG. 2A is an upper perspective view of an example partition that may be disposed within the blood collection device of FIG. 1A, according to some embodiments.
Figure 2B:
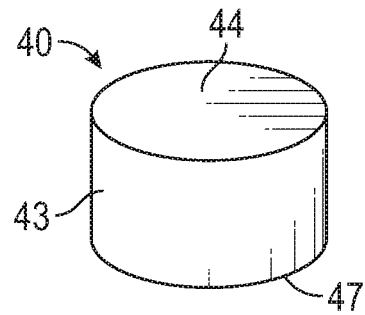
FIG. 2B is a lower perspective view of the partition of FIG. 2A, according to some embodiments.

Referring now to FIGS. 2A-2B, a partition 40 is illustrated. In some embodiments, the partition 40 may be similar or identical to the partition 20 discussed with respect to FIGS. 1A-1E, 3, and 4A-4B in terms of one or more included features and/or operation. In some embodiments, an outer circumference 43 of the partition 40 may contact an inner surface of the tubular container 12 when the partition 40 slides towards the closed end 14. In some embodiments, when the partition 40 slides towards the closed end 14, the partition 40 may maintain a seal between the first chamber 22 and the second chamber 24, which may be airtight. Thus, in some embodiments, the partition 40 may act as a plug.

In some embodiments, a body of the partition 40 may be generally cylindrical. In some embodiments, a proximal face 44 and/or a distal face 47 of the body of the partition 40 may be flat, which may increase a size of the first chamber 22 and/or the second chamber 24. In some embodiments, at least the proximal face 44 may be tapered or rounded, which may facilitate contact between the closed end 14 and the partition 40.

In some embodiments, the partition 40 may be constructed of rubber, which may facilitate sliding of the partition 40 within the tubular container 12 in response to a change in pressure. In other embodiments, the partition 20 may be constructed of a rigid or flexible plastic or another suitable material.

Figure 2C:
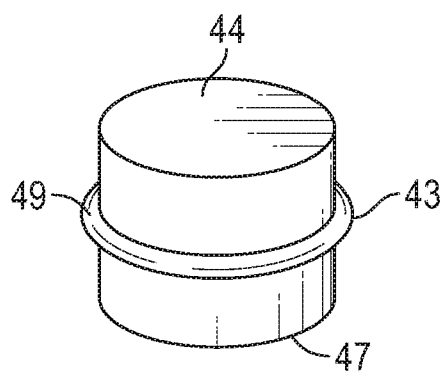
FIG. 2C is an upper perspective view of another example partition that may be disposed within the blood collection device of FIG. 1A, according to some embodiments.

Referring now to FIG. 2C, a partition 48 is illustrated, according to some embodiments. In some embodiments, the partition 48 may be similar or identical to the partition 20 discussed with respect to FIGS. 1A-1E, 3, and 4A-4B, and/or the partition 40 discussed with respect to FIGS. 2A-2B in terms of one or more included features and/or operation. In some embodiments, the partition 48 may include an O-ring 49 coupled to an outer perimeter of the body of the partition 48. In some embodiments, the O-ring 49 may be constructed of rubber and/or the body may be constructed of plastic.

Figure 2D:
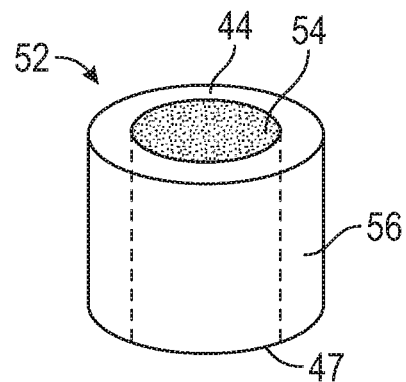
FIG. 2D is an upper perspective view of another example partition that may be disposed within the blood collection device of FIG. 1A, according to some embodiments.

Referring now to FIG. 2D, a partition 50 is illustrated, according to some embodiments. In some embodiments, the partition 50 may be similar or identical in terms of one or more included features and/or operation to one or more of the following: the partition 20 discussed with respect to FIGS. 1A-1E, 3, and 4A-4B, the partition 40 discussed with respect to FIGS. 2A-2B, and the partition 48 discussed with respect to FIG. 2C.

In some embodiments, the partition 50 may include an inner portion 54 and an outer portion 56, which may surround the inner portion 54. In some embodiments, the inner portion 54 may have a first durometer, and the outer portion 56 may have a second durometer. In some embodiments, the first durometer may be greater than the second durometer. In some embodiments, the inner portion 54 and/or the outer portion 56 may be constructed of plastic. In some embodiments, the inner portion 54 may be soft and/or the outer portion 56 may be rigid.

Figure 3:
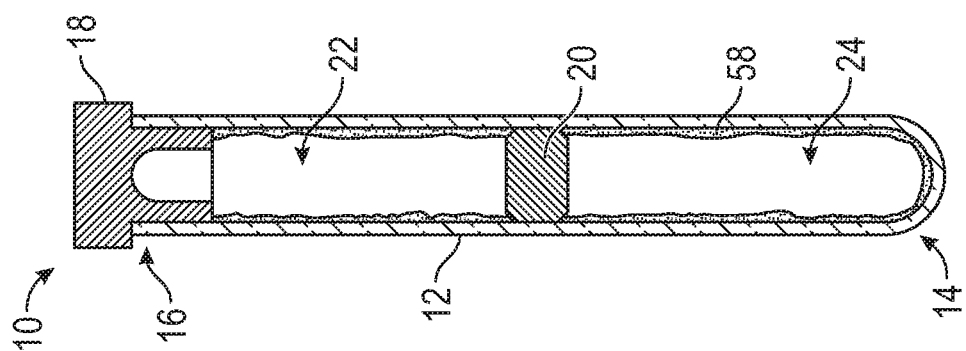
FIG. 3 is another cross-sectional view of the blood collection device of FIG. 1A, according to some embodiments.

Referring now to FIG. 3, in some embodiments, the blood collection device 10 may further include a lubricant 58, which may be disposed on all or a portion of an inner surface of the tubular container 12. In some embodiments, the lubricant 58 may be disposed on all or a portion of the inner surface from the plug 18 to the closed end 14. In some embodiments, the lubricant 58 may be disposed between the partition 20 and the tubular container 12. In some embodiments, the lubricant 58 may include an oil, such as, for example, a silicon oil or a mineral oil. In some embodiments, an amount or location of the lubricant 58 may be modified to adjust an activation pressure. The activation pressure may be defined as a pressure differential between the pressure within the first chamber 22 and the second chamber 24 required to initiate motion of the partition 20 towards the closed end 14 of the tubular container 12. In some embodiments, the pressure differential may be predetermined.

Figure 4B:
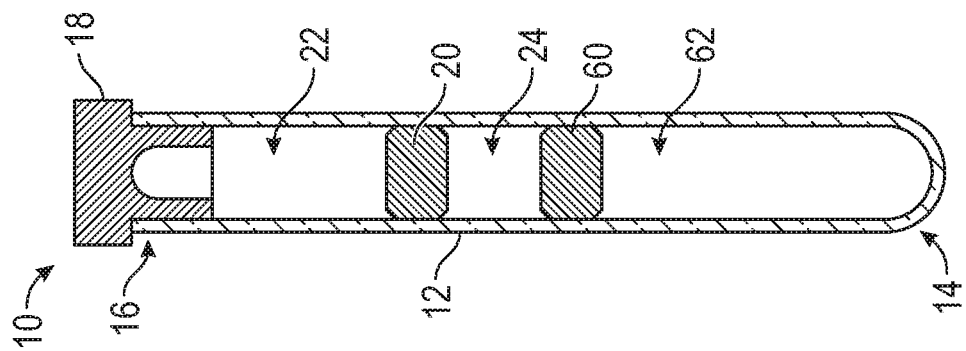
FIG. 4B is a cross-sectional view of the blood collection device of FIG. 4A, according to some embodiments.
Figure 4A:
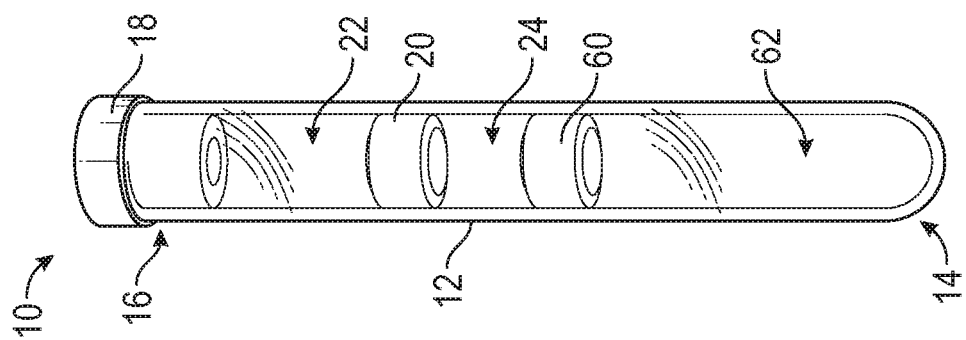
FIG. 4A is an upper perspective view of another blood collection device, according to some embodiments.

Referring now to FIGS. 4A-4B, in some embodiments, the blood collection device 10 may further include another partition 60 and a third chamber 62. In some embodiments, the partition 60 may be similar or identical in terms of one or more included features and/or operation to one or more of the following: the partition 20 discussed with respect to FIGS. 1A-1E, 3, and 4A-4B, the partition 40 discussed with respect to FIGS. 2A-2B, and the partition 48 discussed with respect to FIG. 2C.

In some embodiments, the second chamber 24 may be disposed between the partition 20 and the other partition 60. In some embodiments, the third chamber 62 may also be evacuated, partially or fully, such that a pressure within the third chamber 62 is lower than ambient pressure and equal to the pressure within the first chamber 22 and the pressure within the second chamber 24. In some embodiments, the other partition 60 may be impermeable to air and the third chamber 62 may be airtight. In some embodiments, the partition 20 and the other partition 60 may have different activation pressures. In some embodiments, the blood collection device 10 may include more than two partitions and more than three chambers.

Figure 5B:
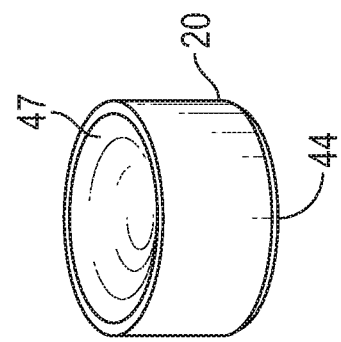
FIG. 5B is an upper perspective view of another example partition that may be disposed within the blood collection device of FIG. 5A, according to some embodiments.
Figure 5A:
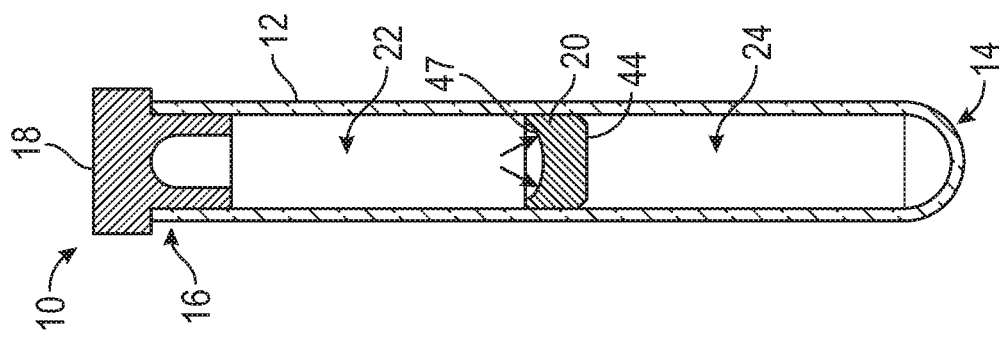
FIG. 5A is another cross-sectional view of the blood collection device of FIG. 1A, according to some embodiments.

Referring now to FIGS. 5A-5B, in some embodiments, the distal face 47 of the body of the partition 40 may include a concave shape. In these embodiments, the distal face 47 may include a circular rim and the concave shape within the rim. In some embodiments, the concave shape may include an inverted dome or another suitable shape. In some embodiments, the distal face 47 of the body may face the first chamber 22. In some embodiments, the concave shape of the distal face 47 may increase friction between the partition 20 and a wall of the tubular container 12, which may contact the partition 40. In further detail, in some embodiments, in response to an increase in pressure within the first chamber 22, a normal force against the concave shape of the distal face 47 may increase, which may push on the concave shape and thereby increase friction between the partition 20 and the wall of the tubular container 12. In some embodiments, the increase in friction between the partition 20 and the wall of the tubular container 12 may slow movement of the partition 20 towards the closed end 14 as the first chamber 22 fills with blood. In some embodiments, the concave shape may be disposed on the distal face 47 and/or the proximal face 44.

Figure 6B:
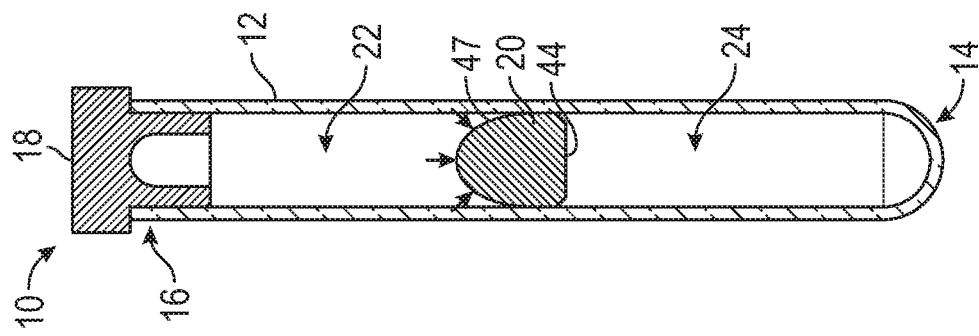
FIG. 6B is a cross-sectional view of the blood collection device of FIG. 6A, according to some embodiments.
Figure 6A:
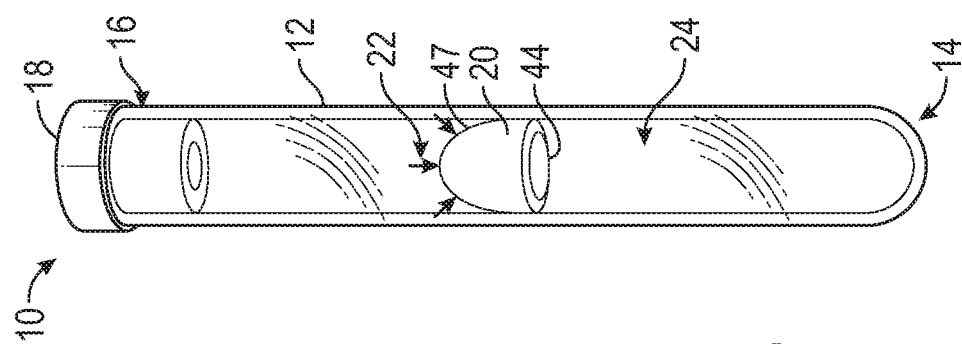
FIG. 6A is another upper perspective view of the blood collection device of FIG. 1A, according to some embodiments.

Referring now to FIGS. 6A-6B, in some embodiments, the distal face 47 of the body of the partition 40 may include a convex shape. In some embodiments, the convex shape may include a dome or another suitable shape. In some embodiments, the distal face 47 of the body may face the first chamber 22. In some embodiments, the convex shape of the distal face 47 may decrease friction between the partition 20 and a wall of the tubular container 12, which may contact the partition 40.

In further detail, in some embodiments, in response to an increase in pressure within the first chamber 22, the normal force against the concave shape of the distal face 47 may increase. In some embodiments, the normal force may push on the convex shape and thereby decrease friction between the partition 20 and the wall of the tubular container 12. In some embodiments, the decrease in friction between the partition 20 and the wall of the tubular container 12 may facilitate or speed movement of the partition 20 towards the closed end 14 as the first chamber 22 fills with blood. In some embodiments, the decrease in friction between the partition 20 and the wall of the tubular container 12 may help overcome an initial resistance of the partition 20 to movement due to stickiness from a lubricant. In some embodiments, the convex shape may be disposed on the distal face 47 and/or the proximal face 44. In some embodiments, the distal face 47 may include the convex shape, and the proximal face 44 may include the concave shape. In other embodiments, the distal face 47 may include the concave shape, and the proximal face 44 may include the convex shape.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A blood collection device, comprising:
  a tubular container comprising a closed end and an open end opposite the closed end;
  a plug sealing the open end; and
  a partition and another partition within the tubular container, wherein the partition and the other partition separate the tubular container into a first chamber, a second chamber, and a third chamber,
  wherein the first chamber is disposed between the plug and the partition, the second chamber is disposed between the partition and the other partition, and the third chamber is disposed between the other partition and the closed end,
  wherein the first chamber, the second chamber, and the third chamber are evacuated such that a pressure within the first chamber, a pressure within the second chamber, and a pressure within the third chamber are lower than ambient pressure,
  wherein the partition and the other partition are impermeable to air and the first chamber, the second chamber, and the third chamber are airtight, and
  wherein in response to coupling the blood collection device to a blood collection set the pressure within the first chamber is configured to increase, and the partition is configured to slide toward the closed end such that the size of the first chamber increases and the size of the second chamber decreases.

2. A method of blood collection, comprising:
  inserting a needle of a blood collection set into a vasculature of a patient, wherein the blood collection set comprises:
    a hub;
    the needle extending distally beyond the hub;
    an adapter, comprising a cannula and an elastomeric sheath, wherein the elastomeric sheath is coupled to the adapter and envelopes the cannula;
    an extension tube, comprising a distal end coupled to the hub and a proximal end coupled to the adapter;
  coupling a blood collection device to the blood collection set by inserting the cannula into the blood collection device, wherein the blood collection device comprises:
    a tubular container comprising a closed end and an open end opposite the closed end;
    a plug sealing the open end; and
    a partition and another partition within the tubular container, wherein the partition and the other partition separate the tubular container into a first chamber, a second chamber, and a third chamber,
    wherein the first chamber is disposed between the plug and the partition, wherein the second chamber is disposed between the partition and the other partition, and the third chamber is disposed between the other partition and the closed end, wherein the first chamber, the second chamber, and the third chamber are evacuated such that a pressure within the first chamber, a pressure within the second chamber, and a pressure within the third chamber are lower than ambient pressure, and wherein the partition and the other partition are impermeable to air and the first chamber, the second chamber, and the third chamber are airtight; and wherein in response to coupling the blood collection device to the blood collection set the pressure within the first chamber increases, and the partition slides towards the closed end such that the size of the first chamber increases and the size of the second chamber decreases.

* * * * *